United States Patent [19]

Mayberry et al.

[11] 4,026,281
[45] May 31, 1977

[54] METHOD AND APPARATUS FOR INSERTING AN INTRAUTERINE CONTRACEPTIVE DEVICE

[75] Inventors: Derral Mayberry, Somerset; Jawahar Sawardeker, Bound Brook; John McShefferty, Somerville, all of N.J.

[73] Assignee: Ortho Pharmaceutical Corporation, Raritan, N.J.

[22] Filed: Oct. 12, 1973

[21] Appl. No.: 405,960

[52] U.S. Cl. ............................................. 128/130
[51] Int. Cl.² ........................................ A61F 5/46
[58] Field of Search ........................... 128/127, 130

[56] References Cited

UNITED STATES PATENTS

| | | | |
|---|---|---|---|
| 3,372,695 | 3/1968 | Beliveau | 128/130 |
| 3,407,806 | 10/1968 | Hulka | 128/130 |
| 3,516,403 | 6/1970 | Coumut | 128/130 |
| 3,533,406 | 10/1970 | Tatum | 128/130 |
| 3,777,748 | 12/1973 | Abramson | 128/130 |
| 3,783,861 | 1/1974 | Abramson | 128/127 |

*Primary Examiner*—Lawrence W. Trapp
*Attorney, Agent, or Firm*—Benjamin F. Lambert

[57] ABSTRACT

A method of inserting an intrauterine contraceptive device is described. The device is mounted in a plunger and the plunger containing the device is inserted into a hollow insertion tube for insertion into the uterine cavity.

3 Claims, 10 Drawing Figures

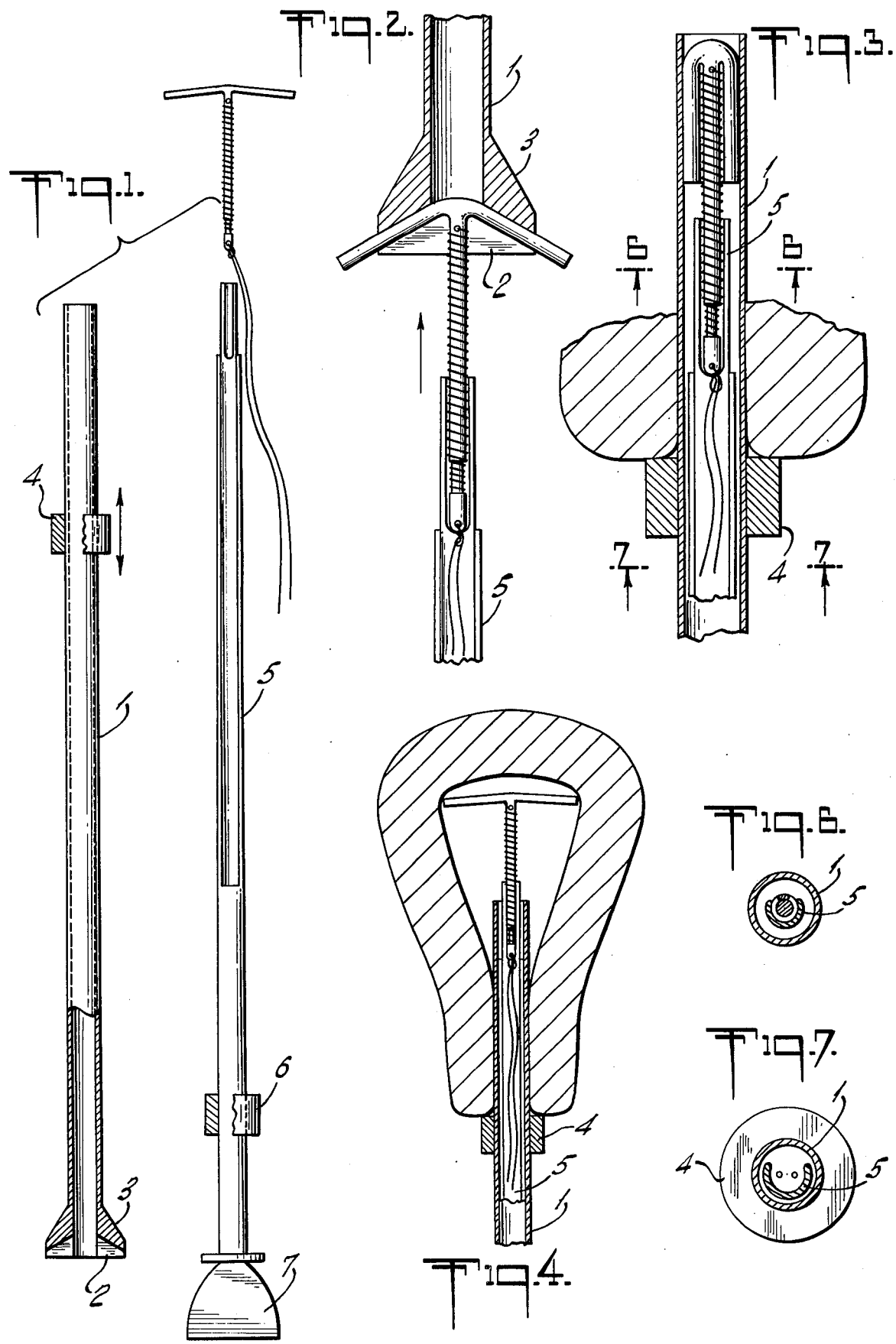

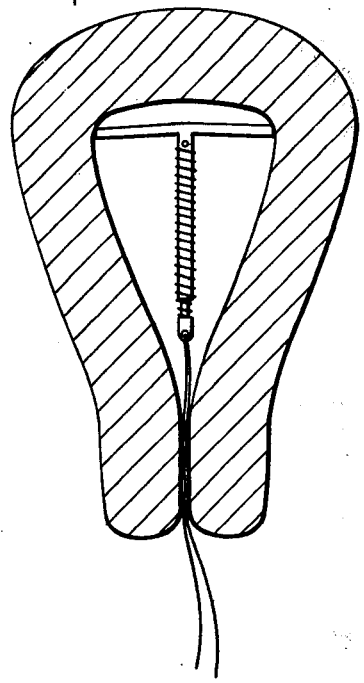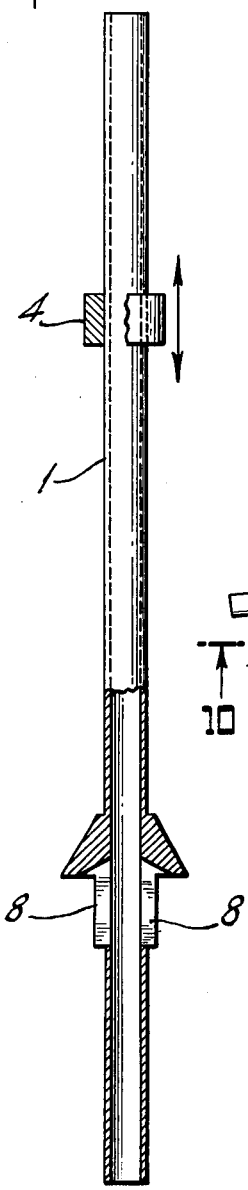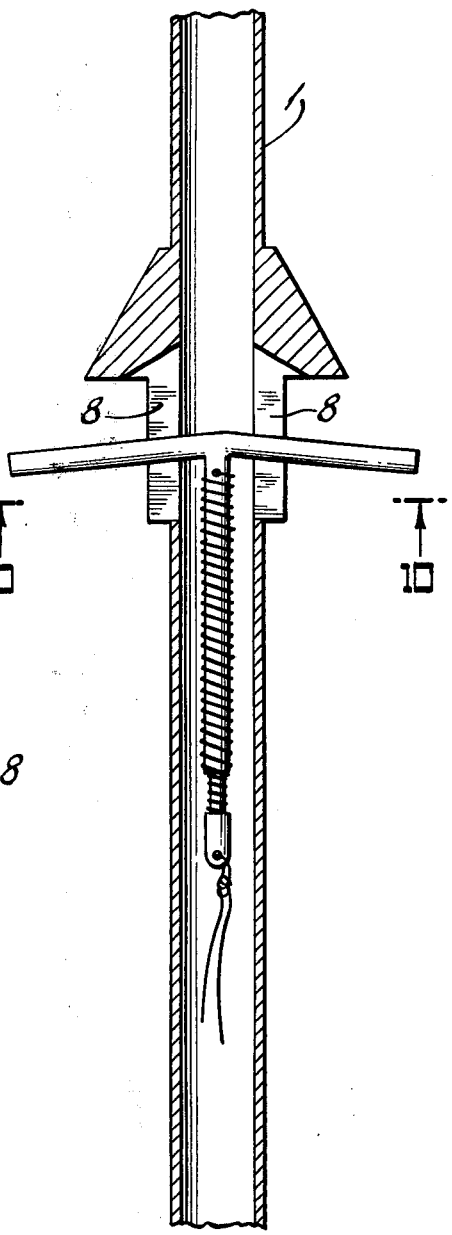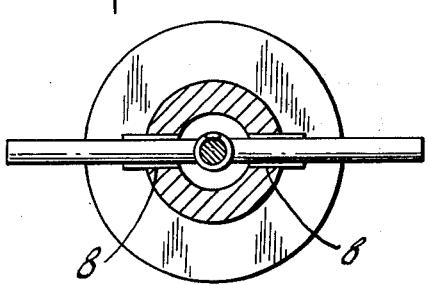

METHOD AND APPARATUS FOR INSERTING AN INTRAUTERINE CONTRACEPTIVE DEVICE

This invention relates to an apparatus for inserting a sterile intrauterine contraceptive device into the uterine cavity and a method of inserting same.

It is known that in a vast majority of cases conception may not occur when a foreign body is present in the uterus. The use of intrauterine devices to prevent pregnancy has recently received a great deal of attention, and a number of preformed configurations have been suggested for such devices. Among these prior art devices are the Lippes "loop", the Margulies "spiral", the Birnberg "bow", the "T", elemental copper or zinc, and various ring configurations.

Various methods have been proposed for introducing the device into the uterine cavity. For example, the Lippes loop is drawn into a hollow rod prior to insertion and then pushed out into the uterine cavity after insertion. Since the configuration is important to the effectiveness of the device, it is not desirable to store the loop in the tube prior to use. The Tatum T device employs an inserter which consists of an elongated tube adapted to be extended through the cervical os and into the uterine cavity. When loaded for implantation, the intrauterine device is placed in the distal end of the inserter tube with the extended arms of the T pressed down along the outer walls of the tube into a pair of in-grooves formed in the sides of the walls. The device is then expelled from the inserter tube by means of a plunger which extends through the inserter. In many of the known methods for inserting an intrauterine device, it is necessary to carry out certain manipulations with the device prior to insertion which may lead to possible contamination of the device and the complications which may follow. Thus, the prior art methods require considerable handling by the physician prior to insertion of the device which is cumbersome and may result in undesirable side effects. There is a need, therefore, for a method of inserting intrauterine devices which eliminates the handling of the device prior to insertion into the uterine cavity.

By the present invention, a method and apparatus for inserting an intrauterine contraceptive device into the uterus are provided which overcome the disadvantages of the prior art methods.

It is, therefore, a primary object of this invention to provide a simple method for inserting an intrauterine contraceptive device of the T-type into the uterus which eliminates the need for handling the device prior to insertion and without the necessity for dilation of the cervix.

This and other objects of the invention will become apparent from the following detailed description taken in connection with the accompanying drawings in which:

FIG. 1 is an exploded elevational view of the component parts of the apparatus.

FIG. 2 is an enlarged fragmentary view of portions of the elements shown in FIG. 1 in the initial stage of insertion.

FIG. 3 is an enlarged fragmentary view of portions of the elements shown in FIG. 1 which illustrates the device in position ready for insertion.

FIG. 4 is an enlarged fragmentary view of portions of the elements which illustrate the device positioned in the uterus just prior to expulsion.

FIG. 5 is a sectional view of the uterine cavity showing the disposition of the intrauterine device therein.

FIGS. 6 and 7 are sectional views taken respectively on 6—6 and 7—7 of FIG. 3.

FIG. 8 is an elevational view of a second embodiment of the inserter of FIG. 1.

FIG. 9 is an enlarged fragmentary view of portions of the elements shown in FIG. 8 which illustrates the device positioned in the inserter tube.

FIG. 10 is a section of FIG. 9 taken along 10—10.

The inserter for inserting the intratuerine device is shown as comprising an elongated hollow tube 1 adapted to be extended through the cervical os into the uterine cavity, said inserter having an external diameter sufficiently small to permit insertion thereof through the cervix usually without the necessity of dilation. In one embodiment of the invention, the insertion tube 1 may be flared at the bottom 2 for easy insertion of the device and is equipped with a non-movable flange 3 also at the bottom to facilitate insertion of devices such as the T or copper T. Alternatively, a molded piece of suitable plastic material of similar design can be physically attached to the bottom end of the inserter tube. The inserter tube may also contain an adjustable stop 4 as shown in FIG. 1. The adjustable stop permits the physician to adjust the length of that portion of the inserter tube which enters the uterine cavity so as not to puncture or damage the cavity walls.

A plunger 5, which is freely slidable within the inserter tube and having a diameter smaller than that of the inserter tube, but adapted to receive the contraceptive device, is also provided for inserting the device into the uterine cavity. The plunger 5 may also be provided with a movable stop 6 to allow the physician to place the device at the end of the inserter tube prior to insertion without pushing the device out of the tube, and an optional handle 7 for easy gripping and manipulation of the tubular element 5 with the fingers.

In order to load the device for insertion into the uterus, it is first placed in the distal end of the plunger 5 as shown in FIGS. 1 and 2. The plunger 5, with the device in position, is then inserted through the bottom of the inserter tube 1 until the device is at the tip of the inserter tube, as shown in FIG. 3. The device is now fully loaded and ready for insertion.

The insertion tube 1, loaded with the device, is then inserted through the cervical os into the uterine cavity. Upon locating the inserter tube in the desired position in the patient, the plunger is then pushed deeper into the inserter tube until the intrauterine device is expelled into the uterine cavity.

In a preferred embodiment of the apparatus, the insertion tube is provided with at least two opposed slots 8 positioned along its length between the end of the tube and the movable stop 4. The opposed slots are particularly useful where devices such as the T are employed. When the T or a similar device is inserted slowly into the inserter tube, the arms of the T will extend out of the slots thus preventing the device from falling out while being handled prior to insertion. The device can be stored in this position and the entire apparatus, including the plunger, can be sterilized prior to use, thus making it unnecessary for the physician to handle the device itself prior to insertion, When the device is to be inserted into the uterus, the inserter tube is inserted through the cervical os and the device is pushed through the inserter tube into the uterine cavity by means of the plunger. In this way there is no need to handle the device before or after insertion and the possibility of contamination due to prior handling is essentially eliminated.

Alternatively, the device can be positioned in the inserter tube by insertion through the slots on the side of the tube. With the device so positioned, the inserter tube containing the device and the plunger can be sterilized prior to ultimate use by the physician. When the device is to be inserted, it is pushed through the inserter tube into the uterine cavity by means of the plunger.

As indicated above, the use of the opposed slots on the inserter tube makes it possible to place the device in position in the inserter tube prior to sterilization. Since the entire insertion apparatus can then be sterilized with the device in position, the physician need only push the plunger through the inserter tube in order to place the device in the uterine cavity. Thus, handling of the device by the physician, as well as possible contamination of the device due to improper handling prior to insertion, are essentially eliminated.

The plunger 5 and insertion tube 1 may be made from conventional materials. Suitable materials which can be employed include, for example, polymeric materials such as polyethylene and polypropylene. While the insertion tube 1 may be made of a rigid material, it is preferably made of a flexible plastic material. The insertion tube may be any suitable shape, but a round or oval shaped tube is preferred. The plunger 5 is preferably made of a flexible material since it must follow the contour of the passage in the inserter tube. The cross section of the plunger 5 corresponds generally to that of the inserter tube 1. The plunger 5 is necessarily longer than the inserter tube 1 so as to be able to push the device completely out of the tube.

The method of this invention is particularly useful for inserting the T or copper T device, but it may be employed with other devices of a similar type.

It will thus be seen that certain changes may be made in carrying out the above invention without departing from the scope of the invention. It is intended that all matter contained in the above description or shown in the accompanying drawings shall be interpreted as illustrative and not limitative of the invention, the scope of which is to be measured by the appended claims.

What is claimed is:

1. A method of inserting an intrauterine contraceptive device which comprises:
    providing a tubular sheath having an outer diameter sufficiently small to permit insertion into the uterus through the cervix, said tubular sheath having at least two opposed slots along its length,
    introducing an intrauterine device into said tubular sheath through said opposed slots, said device being adapted to be within the fold of the uterine cavity,
    introducing a tubular plunger into the bottom of said tubular sheath to a point sufficient to make contact with said device,
    introducing said plunger, tubular sheath and the contained device through the cervix into the uterus,
    expelling said device from said sheath by inserting the plunger deeper into said sheath, whereby said device is in exposed condition within the uterus, and
    withdrawing said sheath.

2. The method of claim 1 wherein the intrauterine contraceptive device is a T.

3. The method of claim 1 wherein the intrauterine contraceptive device is a copper T.

* * * * *